US009110008B2

(12) United States Patent
Baer et al.

(10) Patent No.: US 9,110,008 B2
(45) Date of Patent: Aug. 18, 2015

(54) METHOD FOR ISOTOPIC ANALYSIS OF WATER IN BODILY FLUIDS

(75) Inventors: Douglas Steven Baer, Menlo Park, CA (US); Elena Simone Franklin Berman, Mountain View, CA (US); Manish Gupta, Mountain View, CA (US); David A. Wagner, Nashua, NH (US); Daniel L. Bolt, Medford, MA (US); Susan Lauren Fortson, Mountain View, CA (US)

(73) Assignee: Los Gatos Research, Mountain View, CA (US)

( * ) Notice: Subject to any disclaimer, the term of this patent is extended or adjusted under 35 U.S.C. 154(b) by 504 days.

(21) Appl. No.: 13/191,269

(22) Filed: Jul. 26, 2011

(65) Prior Publication Data
US 2012/0021526 A1    Jan. 26, 2012

Related U.S. Application Data

(60) Provisional application No. 61/367,559, filed on Jul. 26, 2010.

(51) Int. Cl.
*G01N 33/18* (2006.01)
*G01N 21/31* (2006.01)
G01N 21/17 (2006.01)
G01N 21/35 (2014.01)
G01N 21/39 (2006.01)

(52) U.S. Cl.
CPC ............ *G01N 21/31* (2013.01); *G01N 21/1702* (2013.01); *G01N 2021/3595* (2013.01); *G01N 2021/399* (2013.01); *Y10T 436/20* (2015.01)

(58) Field of Classification Search
USPC .................... 436/39, 127–138, 144, 171, 173
See application file for complete search history.

(56) References Cited

U.S. PATENT DOCUMENTS

| 4,158,547 | A |   | 6/1979 | Rousseau et al. |   |
|---|---|---|---|---|---|
| 4,529,879 | A | * | 7/1985 | Schmit | 250/282 |
| 5,135,875 | A |   | 8/1992 | Meucci et al. |   |
| 5,760,189 | A | * | 6/1998 | Vicik et al. | 530/412 |
| 5,783,445 | A | * | 7/1998 | Murnick | 436/35 |
| 5,831,027 | A | * | 11/1998 | McIntosh et al. | 530/382 |
| 6,795,190 | B1 | * | 9/2004 | Paul et al. | 356/437 |
| 6,839,140 | B1 | * | 1/2005 | O'Keefe et al. | 356/436 |
| 7,048,907 | B2 |   | 5/2006 | Groman et al. |   |
| 7,307,059 | B2 |   | 12/2007 | Hellerstein |   |
| 7,435,406 | B2 |   | 10/2008 | Schneider |   |
| 7,449,171 | B2 |   | 11/2008 | Hellerstein |   |
| 7,468,797 | B1 | * | 12/2008 | O'Keefe et al. | 356/437 |
| 7,504,233 | B2 |   | 3/2009 | Hellerstein |   |
| 7,618,827 | B2 |   | 11/2009 | Steven |   |
| 2002/0118364 | A1 | * | 8/2002 | Amonette et al. | 356/436 |
| 2004/0081994 | A1 |   | 4/2004 | Hellerstein |   |
| 2006/0020440 | A1 |   | 1/2006 | Hellerstein |   |
| 2006/0084180 | A1 | * | 4/2006 | Paldus et al. | 436/171 |
| 2007/0248540 | A1 |   | 10/2007 | Hellerstein |   |
| 2008/0221412 | A1 | * | 9/2008 | Baker et al. | 600/310 |
| 2009/0305322 | A1 |   | 12/2009 | Hegg et al. |   |
| 2010/0322865 | A1 | * | 12/2010 | Duerk et al. | 424/9.3 |

OTHER PUBLICATIONS

Turner, M. D. et al, Journal of Applied Physiology 1960, 15, 309-310.*
Zweens, J. et al, Pflugers Archives 1980, 385, 71-77.*
Lukaski, H. C. et al, American Journal of Clinical Nutrition 1985, 41, 363-370.*
Fusch C. et al, Journal of Clinical Chemistry and Clinical Biochemistry 1988, 26, 715-721.*
Shakar, J. J. et al, Analytical Chemistry 1988, 58, 1460-1461.*
Kahled, M. A. et al, Metabolism 1995, 44, 1-3.*
Kerstel, E. R. T. et al, Analytical Chemistry 1999, 71, 5297-5303.*
Aslani, A. et al, Annals of the New York Academy of Science 2000, 904, 287-289.*
van Trigt, R. et al, Analytical Chemistry 2001, 73, 2445-2452.*
Robinson, M. P. et al, Physics of Medicine and Biology 2003, 48, 113-125.*
Kerstel, E. R. T. et al, Spectrochimica Acta A 2002, 58, 2389-2396.*
Van Trigt, R. et al, Journal of Applied Physiology 2002, 93, 2147-2154.*
Rusciano, G. et al, Optics and Lasers in Engineering 2006, 44, 711-721.*
Kerstel, E. R. T. et al, Applied Physics B 2006, 85, 397-406.*
Richman, B. A. et al, Conference on Lasers and Electro-Optics, 2006 and 2006 Quantum Electronics and Laser Science Conference, CLEO/QELS 2006, pp. 1-2.*
Lis, G. et al, Analytical Chemistry 2008, 80, 287-29.*
Kerstel E. et al, Applied Physics B 2008, 92, 439-449.*
Wassenaar, L. I. et al, Environmental Science and Technology 2008, 42, 9262-9267.*
Liu, A. et al, Journal of Quantitative Spectroscopy & Radiative Transfer 2009, 110, 1781-1800.*
Brand, W. A. et al, Rapid Communications in Mass Spectromtery 2009, 23, 1879-1884.*
Schmidt, M. et al, Rapid Communications in Mass Spectromtery 2021, 26, 141-153.*
Rebouche, C. J. et al, American Journal of Clinical Medicine 1987, 45, 373-380.*

(Continued)

*Primary Examiner* — Arlen Soderquist
(74) *Attorney, Agent, or Firm* — Thomas Schneck; Mark Protsik

(57) ABSTRACT

Biological fluid samples containing proteins (e.g., blood plasma or saliva) are prepared for isotopic analysis by precipitating the proteins while leaving the isotopic ratio unaffected. This precipitation can involve adding metal ions, salts, organic solvents, or organic polymers. The sample is then centrifuged to allow transfer of the supernatant for isotopic analysis, e.g. by tunable diode laser absorption spectrometry to obtain a quantitative measure of the $^2H$ and $^{18}O$ isotope levels in the water relative to reference standards.

16 Claims, No Drawings

(56) References Cited

OTHER PUBLICATIONS

Blagojevic, N. et al, Australasian Physical & Engineering Sciences in Medicine 1990, 13, 110-116.*
Brans, Y. W. et al, Clinical Chemistry 1990, 36, 1823-1825.*
Fusch, C. et al, European Journal of Clinical Chemistry and Clinical Biochemistry 1993, 31, 639-644.*
Paton, N. I. et al, Nutrition 1998, 14, 658-666.*
Jennings, G. et al, Clinical Chemistry 1999, 45, 1077-1081.*
Ferrier, L. et al, The Journal of Nutrition 2002, 132, 1725S-1727S.*
Lis, G. et al, Analytical Chemistry 2008, 80, 287-293.*
Medoua, G. N. et al, Clinical Nutrition 2008, 27, 881-888.*
Printout: E Berman et al., High-Frequency Field Deployable Isotope Analyzer for Hydrological Applications, LGR GU2010-5405-BG99, Oregon State University, 1 page.
Printout: Los Gatos Research, Liquid Water Isotope Analyzer (LWIA-24d), 2 pages.
Technical paper 905, "Measuring Energy Expenditure Using the Doubly Labeled Water Method", 7 pages, 2009.
P. Scott, "High-Performance Liquid-Chromatographic Measurement of Plasma Creatinine in Newborns", Clinical Chemistry, vol. 38, No. 1, 1992, pp. 101-103.
J. Kuan et al., "Determination of Plasma Glucose with Use of a Stirrer Containing Immobilized Glucose Dehydrogenase", Clinical Chemistry, vol. 23, No. 6, 1977, pp. 1058-1061.
A. Ghasemi et al., "Protein Precipitation Methods Evaluated for Determination of Serum Nitric Oxide End Products by the Griess Assay", Journal of Medical Sciences Research, 2007, vol. 2, pp. 29-33.
Technical paper 915, "Measurement of Total Body Water, Extracellular and Intracellular Water", Metabolic Solutions, Inc., 2009, 13 pages.
K. Nagy, "Review: Field Metabolic Rate and Body Size", Journal of Experimental Biology, 208, 2005, pp. 1621-1625.
M. Somogyi, "Determination of Blood Sugar", Laboratory of the Jewish Hospital of St. Louis, St. Louis, May 28, 1945, pp. 69-73.
J. DeLany et al., "Energy Expenditure and Substrate Oxidation Predict Changes in Body Fat in Children", Amer. Society of Nutrition, 2006, 84, pp. 862-870.
C. Polson et al., "Optimation of Protein Precipitation Based Upon Effectiveness of Protein Removal and Ionization Effect in Liquid Chromatography—tandem mass spectrometry", Journal of Chromatography B, 785, 2003, pp. 263-275.
I. Bederman et al., "Novel application of the 'doubly labeled' water method: Measuring CO2 production and the tissue-specific dynamics of lipid and protein in vivo", American Journal Physiol Endocrinol Metab 290, 2006, pp. E1048-E1057.
D. Baer et al., "Sensitive Absorption Measurements in the Near-infrared Region Using Off-axis Integrated-cavity-output Spectroscopy", Los Gatos Research, Applied Physics B, 2002, 5 pages.
J. Paul et al., "Ultrasensitive Absorption Spectroscopy with a High-Finesse Optical Cavity and Off-axis Alignment", Applied Optics, vol. 40, No. 27, Sep. 2001, pp. 4904-4910.
H. Binder et al., "The Effect of Metal Cations on the Phase Behavior and Hydration Characteristics of Phospholipid Membranes", Chemistry and Physics of Lipids, 115, 2001, pp. 39-61.
Training Course Series No. 35, "Laser Spectroscopic Analysis of Liquid Water Samples for Stable Hydrogen and Oxygen Isotopes", Int'l Atomic Energy Agency, Vienna, 2009, 45 pages.
A.G. West et al., "Discrepancies between isotope ratio infrared spectroscopy and isotope ratio mass spectrometry for the stable isotope analysis of plant and soil waters", Rapid Communications in Mass Spectrometry, Apr. 2010, 24, pp. 1948-1954.
Ellis et al., "Selected Body Composition Methods Can be Used in Field Studies", Journal of Nutrition 2001, 131, 1589S-1595S.
Schoeller et al., "Analytic Requirements for the Doubly Labeled Water Method", Obesity Research, vol. 3, Supple. 1, Mar. 1995, 15-20.
Schoeller et al., "Energy expenditure by doubly labeled water: validation in humans and proposed calculation", American Journal of Physiology 1986, 250, R823-R830.

* cited by examiner

METHOD FOR ISOTOPIC ANALYSIS OF WATER IN BODILY FLUIDS

CROSS-REFERENCE TO RELATED APPLICATION

The present application claims priority under 35 U.S.C. 119(e) from prior U.S. Provisional Application No. 61/367,559, filed Jul. 26, 2010.

STATEMENT REGARDING FEDERALLY SPONSORED RESEARCH OR DEVELOPMENT

This invention was made with government support under contract number R44RR023231-03 awarded by the National Institutes of Health. The government has certain rights in the invention.

TECHNICAL FIELD

The present invention relates to isotopic analysis of water obtained from saliva, blood plasma, and other biological samples.

BACKGROUND ART

In the field of stable isotope measurements for medical diagnostics, the rate of change of the isotopic ratios is used to study energy expenditure, metabolic studies, and glucose metabolism. In order to analyze a blood sample, it must first be fractionated into blood plasma (approx. 55%) and cellular material (i.e., erythrocytes, leukocytes and platelets, approx. 45%), usually by centrifugation, and then the extracted blood plasma must be further processed so as to remove the albumin, fibrinogen, immunoglobulin and other proteins that would otherwise tend to clog the analysis equipment. Likewise, although saliva is 98% water, glycoproteins such as mucins, as well as various protein enzymes, are present that may need to be removed prior to analysis. Several techniques are known for separating or removing protein, or otherwise extracting the water content from biological samples for analysis.

Conventional measurement technologies, which rely on using isotope ratio mass spectrometry, require conversion of the sample into a gas that can be isotopically characterized (e.g. $H_2$, HD, $D_2$, $O_2$ and $CO_2$). Thus, previous measurements of isotopic ratios of water in blood plasma or saliva typically involved extensive sample conditioning including distillation or direct sample conversion. Distillation is time consuming and onerous, and, because water of different isotopic compositions do not boil or evaporate at equal rates, if distillation is, to be used in preparation for quantitative analysis, then the sample must be distilled to completion so as to extract all of the water from the sample. Otherwise, the isotopes will fractionate and the measurement of the isotopic ratio will be inaccurate. Alternatively, the water in the sample can be converted to another species that is free of contaminants. For example, for $^{18}O/^{16}O$ measurements, the liquid sample can be equilibrated with $CO_2$, and the $CO_2$ can be measured using isotope ratio mass spectrometry to determine the $^{18}O^{16}O$ ratio of the water in the original liquid sample. Similarly, for $^2H/^1H$ measurements, the liquid sample can be reduced to $H_2$ and HD using a hot zinc or chromium catalyst bed.

Recently, optical spectroscopy (e.g. tunable diode laser absorption spectrometry, cavity ringdown spectrometry, off-axis integrated cavity output spectrometry, and photoacoustic spectrometry) has been used to characterize the $^2H/^1H$, $^{18}O/^{16}O$ and $^{17}O/^{16}O$ isotope ratios of water. In this technique, the water is measured directly without any sample conversion. This allows for direct characterization of slightly contaminated samples (e.g. seawater, groundwater, or urine) with minimal to no conditioning. However, these optical analyzers still exhibit difficulties in measuring blood plasma and saliva due to aggregation of the proteins inside the analyzer and sample handling equipment (syringes, evaporation blocks, etc.). This accumulation results in substantial measurement memory and large measurement inaccuracies.

Therefore, a simple and rapid method to remove these proteins without changing the isotope ratio of the liquid sample would enable optical analyzers to characterize the isotope ratios of bodily fluids in a simple, cost-effective and timely manner.

There are several methods of precipitating proteins, including "salting out" the protein, adding organic solvents to reduce the activity of water, adding organic polymers, acidifying the sample to form insoluble salts, and metal-induced affinity precipitation. Many of these techniques can be used to precipitate proteins for isotope studies.

"Salting out" the proteins is based on the principle that proteins are less soluble at higher salt concentrations. The added reagent or salt is often ammonium sulfate or sodium citrate, but other salts including both potassium and sodium sulfates and phosphates are also used as the precipitation reagent. The amount of protein precipitation (or the concentration of salt needed to be added) for a given choice of salt is indicated by the Hofmeister (or lyotropic) series: $citrate^{3-}$>$tartrate^{2-}$≈$SO_4^{2-}$>$HPO_4^{2-}$>$F^-$>$acetate^-$> $HCO_3^-$>$Cl^-$>$Br^-$>$I^-$>$NO_3^-$>$ClO_3^-$>$ClO_4^-$ for anions, and $N(CH_3)_4^+$>$Rb^+$>$NH_4^+$>$K^+$>$Na^+$>$Li^+$>$H^+$>$Mg^{2+}$>$Ca^{2+}$> $Cu^{2+}$>$Zn^{2+}$>$Al^{3+}$ for cations, with precipitation tending to be increased for choices of anions and cations of the salt which occur earlier in the series. The sample may then be centrifuged to separate the proteins from the remaining liquid (mostly water) so as to facilitate subsequent measurements. This salting technique is used for fluid sample preparation in a variety of analytical contexts, including the measurement of $NO_x$, glucose and creatine in blood plasma. However, some salts are inapplicable for isotope studies due to hydrogen-exchange with the liquid sample (e.g. ammonium salts, bicarbonates and other species with terminal exchangeable hydrogen). Moreover, high concentrations of salts are typically required, making it difficult for isotope analyzers to handle repeated samples due to their high salinity. Finally, even at high levels, "salting out" only removes at most 90% of the protein content of a sample, leaving the remaining 10% in solution and still confounding the sample processing.

Another technique, known as the Cohn process, adds ethanol or another organic solvent to the sample fluid so as to precipitate the proteins. This method is more commonly used to fractionate the proteins themselves, with different proteins precipitating out of a sample as the alcohol content increases and pH decreases. Other organic substances (e.g. methanol, acetone, ethylene glycol, trichloroacetic acid (TCA), and hydrazine) can be used in place of the ethanol, particularly where the interest is in the water rather than the protein content and one is not concerned whether or not the proteins are denatured. However, for most of these substances, the technique has the major drawback that the isotope ratio of the water will be changed by hydrogen exchange. Even if the isotope ratio of the substance(s) being added is known, control samples are used, and care is taken that all samples are treated identically, especially the amount of the added material, and computations are made to compensate for the change in isotope ratio, the accuracy of the result may still be adversely affected. Thus, this technique is limited to select solvents that do not exhibit hydrogen exchange (e.g. acetone, other ketones, dioxins and ethers).

A similar method involves adding an organic polymer to the solution to precipitate proteins. This soluble polymer, typically polyethylene glycol, usually has terminal, exchangeable hydrogens that alter the isotope ratio of the fluid. Therefore, this technique is typically unsuitable for isotope studies.

Another protein precipitation method involves adding acid to the solution to form insoluble salts with the amino groups in the protein. Again, this method is unsuitable for isotope studies due to hydrogen exchange of the terminal hydrogen in the added acid.

Yet another technique, flocculation, involving the addition of alginates, carrageenan, or tannins to separate the proteins, is little used. It also suffers the same drawback of changing the isotope ratio as the Cohn process and its variants.

The most promising method of precipitating proteins for isotope analysis involves metal-induced affinity precipitation. This technique involves adding a metal cation (e.g. Zn, Cu, Ca, Al) that forms protein cross-links and results in precipitation. The method is especially well-suited to isotope studies, because it involves a minimal quantity of the metal salt (thus minimizing salinity effects) and does not affect the isotope ratio of the sample (the counter-anion is typically sulfate or chloride, neither of which has exchangeable hydrogen).

Several research groups have used the aforementioned techniques to purify proteins (cf. R. K. Scopes, "Protein Purification: Principles and Practice", $3^{rd}$ ed., Springer, New York, 1994); however, very little work has focused on analysis of the remaining liquid, and there have been no known previous efforts involving characterization of the isotope ratios of that remaining liquid.

A. Ghesemi et al ["Protein Precipitation Methods Evaluated for Determination of Serum Nitric Oxide End Products by the Griess Assay", J Medical Sciences Research, vol. 2, pp. 29-32 (Nov. 15, 2007)] disclose that deproteinization is necessary in $NO_x$ measurement of blood serum samples. Acetonitrile and zinc sulfate with ultrafiltration is the disclosed preferred method of deproteinization used by Ghesemi.

Zinc sulfate or other zinc salt together with methanol and ethylene glycol is the protein precipitation reagent disclosed in U.S. Pat. No. 5,135,875 of Meucci et al.

Zinc sulfate and barium hydroxide are used in the deproteinization method of both M. Somogyi ["Determination of Blood Sugar", J Biological Chemistry, vol. 160, pp. 69-73 (1945)] and J. W. Kuan et al ["Determination of Plasma Glucose with Use of a Stirrer Containing Immobilized Glucose Dehydrogenase", Clinical Chemistry, vol. 23, no. 6, pp. 1058-1061 (1977)] for the determination of plasma glucose (blood sugar).

SUMMARY DISCLOSURE

In the present invention, a sample of blood, saliva or other bodily fluid that may have contained isotope-labeled target metabolites (glucose, doubly-labeled water, etc.) is obtained from a test subject (human or animal). If administered to a test subject, the isotopic tags in the glucose or other metabolite may then contain different ratios of $^{18}O/^{16}O$ and $^2H/^1H$ from their natural abundance, and indeed may be "heavy" glucose containing only $^{18}O$ and $^2H$. When metabolized, these isotopes end up as part of the water in the bodily fluid sample. Any metabolite (sugars, fats, alcohol) that contains abundant hydrogen and oxygen atoms in their molecules and that produces water when broken down in the body could be used. Alternatively, for baseline isotope characterization, no isotope label is administered. Such unlabeled experiments are useful in identifying the diet or travel history of test subjects through the naturally occurring variation in isotopic abundances in their bodily fluids.

After obtaining a sample, proteins in the sample fluid are then precipitated by a method suitable for isotope studies, such as metal-induced affinity, "salting out", or adding organic reagents. For example, the metal-induced affinity method involves adding zinc sulfate ($ZnSO_4$) alone. The precipitate is then separated from the water by centrifugation. Any added reagent that would alter the isotope ratios to be measured must be avoided. This sample preparation using deproteinization in place of evaporation or sample conversion greatly simplifies and speeds up the overall process in the context of doubly-labeled isotopic measurements for metabolic analysis and baseline bodily fluids isotope characterization.

After the precipitation and centrifugation, the isotopic ratios of the water are directly measured by optical spectrometry. This technology has several variants, including tunable diode laser absorption spectrometry, cavity-enhanced absorption spectrometry (including cavity ringdown spectroscopy, integrated cavity output spectroscopy, off-axis integrated cavity output spectroscopy, and cavity-attenuated phase-shift spectroscopy), and photoacoutic specrometry. The liquid water isotope analyzer determines the isotope ratios $^{18}O/^{16}O$, $^{17}O/^{16}O$, and $^2H/^1H$. This technique enables ultrasensitive absorption spectroscopy measurements of $\delta^2H$, $\delta^{17}O$ and $\delta^{18}O$ of water directly from liquid or discrete vapor samples with the highest precision and speed. For labeled experiments, the change of isotopic ratio in the water component of the sample can be related to the metabolic rate or total energy expenditure.

DETAILED DESCRIPTION

One or more samples of blood, saliva or other protein-containing bodily fluid having contained isotope-labeled target metabolites (glucose, etc.) are obtained from one or more test subjects (human or animal). The samples undergo a preparation procedure that involves protein precipitation by metal-induced affinity with zinc sulfate alone, followed by centrifugation. Using pipettes or the like, add 30-250 µL (typ. 200 µL) of each sample to corresponding microcentrifuge tubes (each typically having 1.5 mL·capacity). Then, using a spatula tip, add approximately 5 mg of zinc sulfate monohydrate to each sample. Close the cap of each microcentrifuge tube and vortex all tubes for 15 seconds using a vortex mixer. Place the microcentrifuge tubes into a centrifuge and run at approximately 8000 rpm for about 10 minutes.

Once the centrifuge has stopped, using pipettes or the like, transfer 10-75 µL supernatant of the prepared sample into conical glass inserts of respective autosampler vials (typically each having 1.8 mL capacity), tapping the vials to remove any air bubbles that may have formed in the insert and capping each vial.

For isotopic analysis, in addition to the prepared samples, vials of control samples and laboratory standards are also included. For example, control samples may be baseline samples obtained from the same test subjects prior to dosing with an isotopic metabolite or from other test subjects not subject to the isotopic dosing. Laboratory standards contain water of different known levels of $^2H$ or $^{18}O$ enrichment or depletion. Such laboratory standards may be obtained, e.g., from Elemental Analysis, Inc. of Lexington, Ky. USA (e.g., standards 2190-2194) or Metabolic Solutions, Inc. of Nashua, N.H. USA (e.g. standards Tap, C, D and 15) or Cambridge Isotope Laboratories, Inc. of Andover, Mass. USA. The following table shows the expected $\delta^2H$ and $\delta^{18}O$ values of standards that could be used, where the δ values are reported in parts per thousand (per mil) relative to Vienna Standard Mean Ocean Water (VSMOW) of the International Atomic Energy Agency.

| Standard | Expected $\delta^2H$ per mil | Expected $\delta^{18}O$ per mil |
| --- | --- | --- |
| 2194 | −157.12 | −19.64 |
| 2193 | −61.97 | −10.18 |
| Tap | −56.00 | −8.50 |
| 2192 | 4.93 | 0.56 |
| D | 545.80 | 47.83 |
| 2191 | 843.43 | 108.63 |
| 15 | 1303.30 | 118.76 |
| 2190 | 1701.83 | 266.83 |
| C | 2778.64 | 231.27 |

The standards are used for calibration of the measurement. The isotopic ratios of the water are directly measured by a liquid water isotope analyzer, such as that sold by Los Gatos Research, Inc. of Mountain View, Calif. USA. Los Gatos Research's Liquid Water Isotope Analyzer (model LWIA-24d) provides measurements of $\delta^{18}O$, $\delta^{17}O$ and $\delta^2H$ of water in liquid and discrete vapor samples with unsurpassed performance. It determines the isotope ratios $^{18}O/^{16}O$, $^{17}O/^{16}O$ and $^2H/^1H$, e.g. by off-axis integrated cavity output spectroscopy (ICOS), as described in U.S. Pat. Nos. 6,795,190, 6,839,140 and 7,468,797. Measurements of $\delta^{18}O$, $\delta^{17}O$ and $\delta^2H$ are typically reported at a speed of 1080 injections per day, which corresponds to 180 total samples per day (at a rate of 6 injections per sample). Test measurements using the sample preparation technique of the present invention and the aforementioned analyzer have showed a linearity of $\delta^2H$ and $\delta^{18}O$ measurement with an R-square correlation coefficient for the linear regression lines of 0.9993 for deuterium and 0.9997 for oxygen-18. Accuracy of the measurements using the reference standards was within 5% of expected values. Intra-run precision was defined by a relative standard deviation of ≤1% for samples with <100 δ per mil and ≤2.0% for samples with >100 δ per mil. Inter-run precision over six days was less than 2.0% for all samples. The measurement was unaffected by changes in sample volume from 10 μL to 75 μL.

What is claimed is:

1. A method of performing isotopic analysis of water from biological fluid samples, comprising:
    obtaining a biological fluid sample, wherein the sample contains water and proteins;
    preparing the sample prior to analysis by precipitating the proteins in the sample, wherein a protein-precipitating agent added to the sample leaves isotope ratios unaffected for all isotopes that have been selected to be analyzed, and centrifuging the sample sufficient to separate precipitated protein from supernatant liquid;
    without using any distillation of the sample or of the supernatant liquid prior to quantitative isotopic analysis, transferring, once the centrifuging has stopped, an amount of supernatant liquid from the centrifuged sample to a vial; and
    conducting a quantitative isotopic analysis of at least one of $\delta^{18}O$, $\delta^{17}O$ and $\delta^2H$ in the undistilled supernatant liquid using laser absorption spectroscopy of water.

2. The method as in claim 1, wherein the volume of sample in a range from 30 μL to 250 μL is inserted into a microcentrifuge tube.

3. The method as in claim 1, wherein precipitating the proteins in the sample involves metal-induced affinity protein precipitation by adding a metal-cation salt to the sample.

4. The method as in claim 3, wherein the metal-cation salt is any of a zinc, copper, calcium or aluminum salt.

5. The method as in claim 4, wherein zinc sulfate monohydrate is added to the sample at a rate of 5 mg per 200 μL of sample, followed by vortexing of the microcentrifuge tube.

6. The method as in claim 1, wherein precipitating the proteins in the sample involves salting the solution with any of a citrate, phosphate or sulfate salt.

7. The method as in claim 1, wherein precipitating the proteins in the sample involves adding an organic solvent incapable of hydrogen exchange to the sample.

8. The method as in claim 7, wherein the organic solvent is selected from any of acetone, ketones, dioxanes and ethers.

9. The method as in claim 1, wherein precipitating the proteins in the sample involves adding an organic polymer agent incapable of hydrogen exchange to the sample.

10. The method as in claim 9, wherein the organic polymer agent is polyethylene glycol.

11. The method as in claim 1, wherein the sample is centrifuged at 5000-10000 rpm for 8-12 minutes.

12. The method as in claim 1, wherein 10 μL to 75 μL of supernatant liquid is transferred to a vial for measurement.

13. The method as in claim 1, wherein the quantitative analysis is calibrated using one or more reference standards.

14. The method as in claim 1, wherein the quantitative analysis is conducted using cavity-enhanced absorption spectroscopy.

15. The method as in claim 14, wherein the cavity-enhanced absorption spectroscopy is selected from any of cavity ringdown spectroscopy, integrated cavity output spectroscopy, off-axis integrated cavity output spectroscopy, and cavity-attenuated phase-shift spectroscopy.

16. The method as in claim 1, wherein the laser absorption spectroscopy for conducting quantitative analysis of the sample is any of photoacoustic spectroscopy, and photothermal spectroscopy.

* * * * *